US010670574B2

United States Patent
Rapoport et al.

(10) Patent No.: US 10,670,574 B2
(45) Date of Patent: Jun. 2, 2020

(54) NMR-BASED SYSTEMS FOR CRUDE OIL ENHANCEMENT AND METHODS THEREOF

(71) Applicant: ASPECT INTERNATIONAL (2015) PRIVATE LIMITED, Singapore (SG)

(72) Inventors: Uri Rapoport, Moshav Ben Shemen (IL); Tal Cohen, Herzlia (IL)

(73) Assignee: ASPECT INTERNATIONAL (2015) PRIVATE LIMITED, Singapore (SG)

(*) Notice: Subject to any disclaimer, the term of this patent is extended or adjusted under 35 U.S.C. 154(b) by 75 days.

(21) Appl. No.: 15/544,268

(22) PCT Filed: Jan. 17, 2016

(86) PCT No.: PCT/IL2016/050052
§ 371 (c)(1),
(2) Date: Jul. 18, 2017

(87) PCT Pub. No.: WO2016/116926
PCT Pub. Date: Jul. 28, 2016

(65) Prior Publication Data
US 2018/0011073 A1    Jan. 11, 2018

Related U.S. Application Data

(60) Provisional application No. 62/104,863, filed on Jan. 19, 2015.

(51) Int. Cl.
*G01N 33/28* (2006.01)
*G01N 24/08* (2006.01)
(Continued)

(52) U.S. Cl.
CPC ......... *G01N 33/2823* (2013.01); *C10G 15/00* (2013.01); *C10G 15/08* (2013.01);
(Continued)

(58) Field of Classification Search
CPC .... G01N 33/2823; G01N 11/00; G01N 13/02; G01N 24/08; G01N 24/81; G01N 24/85
See application file for complete search history.

(56) References Cited

U.S. PATENT DOCUMENTS 2,768,529 A    10/1956 Hagler, Sr.
3,175,403 A    3/1965 Nelson
(Continued)

FOREIGN PATENT DOCUMENTS

CN    1236478    11/1999
CN    1291873    4/2001
(Continued)

OTHER PUBLICATIONS

Bradley Jr. et al., The appearance of rapidly flowing blood on magnetic resonance images, AJR, Dec. 1984, 143:1167-1174.
(Continued)

*Primary Examiner* — Dominic E Hawkins
(74) *Attorney, Agent, or Firm* — Loeb & Loeb LLP (57) ABSTRACT

An NMR-based system (10) to analyze one or more of the following: (i) crude oil property, (ii) crude oil rheology of crude oil, comprising an NMR device (11) for providing time and/or batch resolved NMR analysis and/or crude oil rheological profile, said NMR having a crude oil inflow pipe (13), and is in a fluid connection (14) with a crude oil refinery facility (12); wherein said system further comprising a computer readable medium configured to store a retrievable crude oil NMR analysis and/or crude oil rheological profile of a desired crude oil product (standard crude oil product, SCOP), thereby providing said system means to compare NMR analysis and/or crude oil rheological profile of said SCOP with said time or batch resolved crude oil.

13 Claims, 3 Drawing Sheets

(51) Int. Cl.
  *C10G 15/00* (2006.01)
  *G01N 11/00* (2006.01)
  *C10G 15/08* (2006.01)
  *G01N 13/02* (2006.01)

(52) U.S. Cl.
  CPC .............. *G01N 11/00* (2013.01); *G01N 13/02* (2013.01); *G01N 24/08* (2013.01); *G01N 24/081* (2013.01); *G01N 24/085* (2013.01); *C10G 2300/1033* (2013.01); *C10G 2300/302* (2013.01)

(56) References Cited

U.S. PATENT DOCUMENTS

| | | |
|---|---|---|
| 3,989,630 A | 11/1976 | Walker |
| 4,417,474 A | 11/1983 | Elderton |
| 4,468,622 A | 8/1984 | Frese et al. |
| 4,697,594 A | 10/1987 | Mayo, Jr. |
| 4,904,603 A | 2/1990 | Jones et al. |
| 4,994,746 A | 2/1991 | Panosh |
| 5,023,551 A | 6/1991 | Kleinberg et al. |
| 5,145,189 A | 9/1992 | Pope |
| 5,161,409 A | 11/1992 | Hughes et al. |
| 5,168,226 A | 12/1992 | Hinks |
| 5,208,534 A | 5/1993 | Okamoto et al. |
| 5,280,243 A | 1/1994 | Miler |
| 5,306,909 A | 4/1994 | Jones et al. |
| 5,479,925 A | 1/1996 | Dumoulin et al. |
| 5,532,593 A | 7/1996 | Maneval et al. |
| 5,557,103 A | 9/1996 | Hughes et al. |
| 5,557,201 A | 9/1996 | Kleinberg et al. |
| 5,696,448 A | 12/1997 | Coates et al. |
| 5,705,927 A | 1/1998 | Sezginer et al. |
| 5,757,187 A | 5/1998 | Wollin |
| 5,784,333 A | 7/1998 | Tang et al. |
| 5,827,952 A * | 10/1998 | Mansure ................ G01N 11/00 73/61.45 |
| 5,986,454 A | 11/1999 | Leifer |
| 6,069,106 A * | 5/2000 | Hettinger, Jr. ......... B01J 29/076 502/64 |
| 6,090,728 A | 7/2000 | Yenni, Jr. et al. |
| 6,107,796 A | 8/2000 | Prammer |
| 6,178,807 B1 | 1/2001 | Baldwin et al. |
| 6,215,304 B1 | 4/2001 | Slade |
| 6,268,726 B1 | 7/2001 | Prammer et al. |
| 6,362,619 B2 | 3/2002 | Prammer et al. |
| 6,412,337 B1 | 7/2002 | Arzate et al. |
| 6,421,337 B1 | 7/2002 | Rao et al. |
| 6,452,390 B1 | 9/2002 | Wollin |
| 6,507,191 B1 | 1/2003 | Eguchi et al. |
| 6,518,758 B1 | 2/2003 | Speier et al. |
| 6,549,007 B1 | 4/2003 | Hills et al. |
| 6,550,327 B1 | 4/2003 | Van Berk |
| 6,646,437 B1 | 11/2003 | Chitale et al. |
| 6,807,857 B2 | 10/2004 | Storm, Jr. et al. |
| 6,856,132 B2 | 2/2005 | Appel et al. |
| 6,907,375 B2 | 6/2005 | Guggari et al. |
| 6,913,827 B2 | 7/2005 | George et al. |
| 6,952,096 B2 | 10/2005 | Freedman |
| 7,075,366 B2 | 7/2006 | Deem et al. |
| 7,295,933 B2 | 11/2007 | Gysling et al. |
| 7,352,179 B2 | 4/2008 | Chen et al. |
| 7,486,071 B2 | 2/2009 | Care et al. |
| 7,489,132 B2 | 2/2009 | Arik et al. |
| 7,570,058 B1 | 8/2009 | Wong et al. |
| 7,823,656 B1 | 11/2010 | Williams |
| 7,908,034 B2 | 3/2011 | Gray |
| 7,921,731 B2 | 4/2011 | Bajikar et al. |
| 8,024,962 B2 | 9/2011 | Tonmukayakul et al. |
| 8,143,887 B2 | 3/2012 | Pusiol |
| 8,256,532 B2 | 9/2012 | Gray |
| 8,373,412 B2 | 2/2013 | Kruspe et al. |
| 8,461,842 B2 | 6/2013 | Thuringer et al. |
| 8,469,118 B2 | 6/2013 | Passade-Boupat et al. |
| 8,736,263 B2 | 5/2014 | Minh |
| 8,763,170 B1 | 7/2014 | Ungarsohn |
| 8,763,710 B2 | 7/2014 | Graue |
| 8,791,695 B2 | 7/2014 | Balcom et al. |
| 8,807,084 B2 | 8/2014 | Rapoport et al. |
| 8,812,236 B1 | 8/2014 | Freeman et al. |
| 8,851,018 B2 | 10/2014 | Rapoport et al. |
| 8,896,310 B2 | 11/2014 | Rapoport |
| 9,194,972 B2 | 11/2015 | Van Der Zwaag et al. |
| 9,448,093 B2 | 9/2016 | Rapoport |
| 9,476,847 B2 * | 10/2016 | Trygstad ................ G01N 24/08 |
| 2002/0173717 A1 | 11/2002 | Rohling et al. |
| 2003/0006768 A1 * | 1/2003 | Kleinberg ............ G01N 24/081 324/303 |
| 2004/0017193 A1 * | 1/2004 | Speier .................. G01N 24/081 324/303 |
| 2004/0090230 A1 | 5/2004 | Appel et al. |
| 2004/0108852 A1 | 6/2004 | de Swiet |
| 2004/0116799 A1 | 6/2004 | Srinivasan |
| 2004/0127786 A1 | 7/2004 | Schmit et al. |
| 2004/0140800 A1 | 7/2004 | Madio et al. |
| 2004/0169512 A1 | 9/2004 | Jara |
| 2005/0011283 A1 | 1/2005 | Gysling et al. |
| 2005/0024053 A1 | 2/2005 | Care et al. |
| 2005/0030020 A1 | 2/2005 | Siess et al. |
| 2005/0044957 A1 | 3/2005 | Muldowney |
| 2005/0203420 A1 | 9/2005 | Kleen et al. |
| 2006/0011547 A1 | 1/2006 | Bell |
| 2006/0279283 A1 | 12/2006 | Nistler et al. |
| 2007/0061081 A1 | 3/2007 | Moran |
| 2007/0164737 A1 | 7/2007 | Pusiol |
| 2007/0188172 A1 | 8/2007 | Garwood et al. |
| 2008/0136049 A1 | 6/2008 | Sen et al. |
| 2008/0136409 A1 | 6/2008 | Sen et al. |
| 2008/0174309 A1 | 7/2008 | Pusiol et al. |
| 2008/0180226 A1 | 7/2008 | Schmidt |
| 2008/0189456 A1 | 8/2008 | Schmidt et al. |
| 2008/0257413 A1 | 10/2008 | Noureldin et al. |
| 2009/0004748 A1 * | 1/2009 | Ganesan ................ G01N 24/08 436/28 |
| 2009/0044638 A1 | 2/2009 | Gysling et al. |
| 2009/0050318 A1 * | 2/2009 | Kasevich .............. E21B 43/003 166/248 |
| 2009/0050369 A1 | 2/2009 | Pop et al. |
| 2009/0072824 A1 | 3/2009 | Romero |
| 2009/0090504 A1 | 4/2009 | Weightman et al. |
| 2009/0194330 A1 | 8/2009 | Gray |
| 2009/0312963 A1 | 12/2009 | Najim Al-Khamis |
| 2009/0312964 A1 | 12/2009 | Najim Al-Khamis |
| 2010/0133488 A1 | 6/2010 | Giakos |
| 2010/0154325 A1 | 6/2010 | Boesel et al. |
| 2010/0264914 A1 | 10/2010 | Minh |
| 2010/0271019 A1 * | 10/2010 | Anand ................. G01N 24/081 324/303 |
| 2011/0036584 A1 | 2/2011 | Weightman et al. |
| 2011/0125333 A1 | 5/2011 | Gray |
| 2011/0162652 A1 | 7/2011 | Rapoport |
| 2011/0185795 A1 | 8/2011 | Colquhoun |
| 2011/0186049 A1 | 8/2011 | Rapoport |
| 2011/0234347 A1 | 9/2011 | Rapoport |
| 2011/0270525 A1 | 11/2011 | Hunter |
| 2011/0296911 A1 | 12/2011 | Moore et al. |
| 2011/0304333 A1 | 12/2011 | Rapoport |
| 2012/0013335 A1 | 1/2012 | Saasen et al. |
| 2012/0024602 A1 | 2/2012 | Larson |
| 2012/0065491 A1 | 3/2012 | Borgert et al. |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0092007 A1 | 4/2012 | Li et al. |
| 2012/0119742 A1 | 5/2012 | Rapoport |
| 2012/0205288 A1 * | 8/2012 | Jia ........................... B01J 8/007 208/144 |
| 2012/0212224 A1 | 8/2012 | Burns |
| 2012/0265050 A1 | 10/2012 | Wang |
| 2013/0009959 A1 | 1/2013 | Calamante et al. |
| 2013/0025062 A1 | 1/2013 | Esch |
| 2013/0060474 A1 | 3/2013 | Venkataramanan et al. |
| 2013/0079624 A1 | 3/2013 | Rapoport |

(56) References Cited

U.S. PATENT DOCUMENTS

| | | | |
|---|---|---|---|
| 2013/0090855 A1 | 4/2013 | Rasmus et al. | |
| 2013/0091941 A1 | 4/2013 | Huh et al. | |
| 2013/0109956 A1 | 5/2013 | Rapoport | |
| 2013/0123639 A1 | 5/2013 | Ando | |
| 2013/0124106 A1* | 5/2013 | Rogel | G01N 33/2823 702/25 |
| 2013/0154644 A1 | 6/2013 | Virtanen et al. | |
| 2013/0179092 A1 | 7/2013 | Martin et al. | |
| 2013/0237803 A1 | 9/2013 | Rapoport | |
| 2013/0271135 A1 | 10/2013 | Ozen et al. | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2013/0345994 A1 | 12/2013 | Wiklund et al. | |
| 2014/0049257 A1 | 2/2014 | Rapoport | |
| 2014/0050824 A1 | 2/2014 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0099010 A1 | 4/2014 | Rapoport | |
| 2014/0103927 A1 | 4/2014 | Rapoport | |
| 2014/0117989 A1 | 5/2014 | Rapoport | |
| 2014/0128725 A1 | 5/2014 | Rapoport | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0253116 A1* | 9/2014 | Freedman | G01R 33/30 324/303 |
| 2014/0257081 A1 | 9/2014 | Rapoport | |
| 2014/0262957 A1* | 9/2014 | Gong | G01N 33/30 208/291 |
| 2014/0266203 A1 | 9/2014 | Rapoport | |
| 2014/0300358 A1 | 10/2014 | Rapoport | |
| 2014/0309951 A1 | 10/2014 | Alvarez-Vallejos et al. | |
| 2014/0333304 A1 | 11/2014 | Jensen | |
| 2014/0354299 A1 | 12/2014 | Rapoport | |
| 2014/0378821 A1 | 12/2014 | Rapoport et al. | |
| 2014/0378825 A1 | 12/2014 | Rapoport et al. | |
| 2015/0059157 A1 | 3/2015 | Rapoport | |
| 2015/0059655 A1 | 3/2015 | Rapoport | |
| 2015/0065788 A1 | 3/2015 | Rapoport | |
| 2015/0084630 A1 | 3/2015 | Rapoport | |
| 2015/0087051 A1 | 3/2015 | Rapoport | |
| 2015/0112186 A1 | 4/2015 | Rapoport et al. | |
| 2015/0130460 A1* | 5/2015 | Valori | G01N 24/081 324/309 |
| 2015/0137812 A1 | 5/2015 | Rapoport | |
| 2015/0141799 A1 | 5/2015 | Rapoport et al. | |
| 2015/0168519 A1 | 6/2015 | Rapoport | |
| 2015/0268374 A1 | 9/2015 | Rapoport | |
| 2015/0320888 A1 | 11/2015 | Yoneda et al. | |
| 2015/0357694 A1 | 12/2015 | Denis et al. | |
| 2015/0377998 A1 | 12/2015 | Bendel | |
| 2016/0053187 A1* | 2/2016 | Hayasaka | C10G 45/58 208/141 |
| 2016/0108687 A1 | 4/2016 | Rapoport | |
| 2016/0109539 A1 | 4/2016 | Mardor et al. | |
| 2017/0243681 A1 | 8/2017 | Somerkoski et al. | |

FOREIGN PATENT DOCUMENTS

| | | |
|---|---|---|
| CN | 1422324 | 6/2003 |
| CN | 1427877 | 7/2003 |
| CN | 1590994 | 3/2005 |
| CN | 101421636 | 4/2009 |
| CN | 101556234 | 10/2009 |
| CN | 101581717 | 11/2009 |
| CN | 101632584 | 1/2010 |
| CN | 101793147 | 8/2010 |
| CN | 101907586 | 12/2010 |
| CN | 103217362 | 7/2013 |
| CN | 103542899 | 1/2014 |
| CN | 103712071 | 4/2014 |
| CN | 103954639 | 7/2014 |
| DE | 202014105273 | 11/2014 |
| EP | 0 210 289 | 2/1987 |
| EP | 0770660 | 5/1997 |
| EP | 0835463 | 8/2003 |
| EP | 1532460 | 5/2005 |
| EP | 2604996 | 6/2013 |
| EP | 2927420 A2 | 10/2015 |
| EP | 2927420 A3 | 2/2016 |
| GB | 2341685 A | 7/1999 |
| RU | 2229023 | 5/2004 |
| RU | 2285119 | 10/2006 |
| RU | 2367982 | 9/2009 |
| SU | 876954 | 10/1981 |
| SU | 1041677 | 9/1983 |
| WO | WO1995018387 | 7/1995 |
| WO | WO2001002832 | 1/2001 |
| WO | WO01/51588 | 7/2001 |
| WO | WO2001051588 | 7/2001 |
| WO | WO2001051589 | 7/2001 |
| WO | WO2008008447 | 1/2008 |
| WO | WO2008043373 | 4/2008 |
| WO | WO2010000055 | 1/2010 |
| WO | WO2011095600 | 8/2011 |
| WO | WO2012004797 | 1/2012 |
| WO | WO2013009299 | 1/2013 |
| WO | WO2013162400 | 10/2013 |
| WO | WO2013179092 | 12/2013 |
| WO | WO2014004573 | 1/2014 |
| WO | WO2014027350 | 2/2014 |
| WO | WO2014203245 | 12/2014 |
| WO | WO2015070872 | 5/2015 |

OTHER PUBLICATIONS

Yan, Jienian, Drilling Fluids Technology, May 31, 2001, China University of Petroleum Press, pp. 61-66.
ANSI/ISA SP76.00.2002 Miniature, Modular Mechanical Standard Specifications, 2002.
Arola et al., Use of nuclear magnetic resonance imaging as a viscometer for process monitoring, Chemical Engineering Science, 1997, 52(13), 2049-2057.
Bennett, et al. A nondestructive technique for determining thermal properties of thermal barrier coatings, Journal of Applied Physics, 2005, 97, 013520,1-12.
Bird et al. Transport Phenomena, Chapter. 2, Shell momentum balances and velocity distributions in laminar flow, Dec. 31, 2002, XP-002768172, Wiley, p. 54.
Caprihan, et al. Flow measurements by NMR, Physics Reports, (Review Section of Physics Letters)1990, 198, No. 4, 195-235.
Coussot et al., Rheological behavior of drilling muds, characterization using MRI visualization, Oil & Gas Science and Technology, Rev. IFP, 2004, vol. 59, No. 1, 23-29.
Degre et al., Rheology of complex fluids by particle image velocimetry in microchannels, Appl. Phys. Lett. 89(2), 024104, 2006, 1-3.
Doble et al., Optimization of the relaxivity of MRI contrast agents: effects of poly(ethylene glycol) chains on the water-exchange rates of Gd complexes, J. Am. Chem. Soc. 2001, 123, 10758-10759.
Dogan et al., Measurement of polymer melt rheology using ultrasonics-based in-line rheometry, Meas. Sci. Technol.,2005, 16(8):1684-1690.
Dyverfeldt et al., Quantification of intravoxel velocity standard deviation and turbulence intensity by generalizing phase-contrast MRI, Magnetic Resonance in Medicine, 2006, 56:850-858.
Felemban, et al. RFID for Oil and Gas Industry: Applications and Challenges, International Journal of Engineering and Innovative Technology (IJEIT) vol. 3, Issue 5, Nov. 2013, 20-85.
Goloshevsky et al., Nuclear magnetic resonance imaging for viscosity measurements of non-Newtonian fluids using a miniaturized RF coil, Meas. Sci. Technol., 2005, 16:513-518.
Gunnerod et al., Highly automated drilling fluids system improves HSE and efficiency, reduced personnel needs, Drilling Contractor, Heath, Safety & Environment, Jan./Feb. 2009, 73-77.

(56) References Cited

OTHER PUBLICATIONS

Guzel et al., Predicting laminar—turbulent transition in Poiseuille pipe flow for non-Newtonian fluids, Chemical Engineering Science 2009, 64 (2) 254-264.

Hou et al., Review Article, Instrument techniques for rheometry, Review of Scientific Instruments, 2005, 76, 101101, 1-19.

Hsu et al., Encoding to the longitudinal magnetization for MR imaging and flow velocity mapping, Journal of Magnetic Resonance, 2006, 183,41-49.

International Electromechanical Commission in publication, IEC 62339-1:2006, 2006.

Kose, Katsumi, Visualization of local shearing motion in turbulent fluids using echo-planar imaging, Journal of Magnetic Resonance, 1992, 96, 596-603.

Lucas et al., An Iterative Image Registration Technique with an Application to Stereo Vision, Proceedings of Imaging Understanding Workshop, pp. 121-130 (1981).

MacGowan et al., Fast measurements of the motion and velocity spectrum of blood using MR tagging, Magnetic Resonance in Medicine, 2001, 45:461-469.

Ocali et al., Ultimate intrinsic signal-to-noise ratio in MRI, MRM, 1998, 39:462-473.

Pohost et al., Nuclear magnetic resonance imaging: With or without nuclear?, JACC Mar. 1986, vol. 7, No. 3, 709-710.

Poole et al., Development-Length Requirements for Fully Developed Laminar Pipe Flow of Inelastic Non-Newtonian Liquids, Journal of Fluids Engineering, Oct. 2007, vol. 129, 1281-1287.

Poulichet et al., Optimisation and realisation of a portable NMR apparatus and Micro Antenna for NMR, DTIP, May 2011, 11-13, Aix-en-Provence, France.

Prammer et al., The magnetic resonance while-drilling tool: theory and operation, Society of Engineers, 2000, SPE62981, 1-8.

Rabideau et al., The extrusion of a model yield stress fluid imaged by MRI velocimetry, J. Non-Newtonian Fluid Mech, 2010, 165, 394-408.

Shadday Jr., M.A., Recommendations for rheological testing and modelling of DWPF meter feed slurries (U), Engineering & Materials Technology Dept., WSRC-TR-94/0357, 1994 pp. 1-45.

Roelstraete, Koen, Nuclear magnetic resonance analysis on-line; overview of the technology, benefits, solutions and applications to the refinery, Prove Interlaboratorio Prodotti Petroliferi Milano, Nov. 9, 2011, Jan. 29, 2011, pp. 1-52, retrieved from the internet: https://www.innovhub-ssi.it//c/document library/get file?uuid= 2114aca0-95ee-4aa8-bb50-75170b7f0120&groupId=11648 [retrieved on Apr. 30, 2019].

Fumoto, E. et al. Catalytic cracking of heavy oil over a complex metal oxide catalyst in a steam atmosphere, ACS Symposium Series, Jan. 20, 2012, American Chemical Society/Oxford University Press, vol. 1092, pp. 75-85.

Li et al., Pipe flow of aqueous polyacrylamide solutions studies by means of nuclear magnetic resonance imaging, J. Non-Newtonian Fluid Mech., 57 (1995) 155-175.

Macosko, Christopher W., Rheology principles, measurements, and applications, 1994, VCH Publishers, Inc. pp. 1-9.

\* cited by examiner

NMR-BASED SYSTEMS FOR CRUDE OIL ENHANCEMENT AND METHODS THEREOF

FIELD OF THE INVENTION

The present invention relates to NMR-based systems for crude oil enhancement and to methods thereof.

BACKGROUND OF THE INVENTION

Crude oil contains four different hydrocarbons including paraffins, napthenes, aromatics, and asphaltenes. Paraffins, or alkanes, are saturated hydrocarbons that consist only of hydrogen and carbon atoms, having the general formula $CnH2n+2$. All bonds are single bonds, and the carbon atoms are not joined in cyclic structures but instead form a simple chain. They make up from about 15 to about 60% of crude oil, and on average about 30%. Resins or naphthenes, otherwise known as cycloalkanes, are alkanes that have one or more rings of carbon atoms in the chemical structure of their molecules. They make up from about 30 to about 60% of crude oil, and on average about 49%. Aromatics, or arenes, are hydrocarbons with alternating double and single bonds between carbon atoms forming rings. Aromatics make up from about 3 to about 30% of crude oil, and on average about 15%, See Antonio Cardenas et al., US 20130264247 patent application by Nano Dispersions Technology Inc (NDT patent) which is incorporated herein as a reference, Asphaltenes consist primarily of carbon, hydrogen, nitrogen, oxygen, and sulfur, as well as trace amounts of vanadium and nickel. The C:H ratio is approximately 1:1.2, depending on the asphaltene source. Asphaltenes are defined operationally as the n-heptane (C7H16)-insoluble, toluene (C6H5CH3)-soluble component of a carbonaceous material such as crude oil, and are the sticky, black, highly viscous residue of distillation processes. They make up the remainder of crude oil, and on average from about 3 to about 10% of the crude oil; however heavy oils can contain 10% or more, with a high C:H ratio. Due to the aggregation of asphaltenes, they are the most significant contributor to the viscosity of crude oil affecting its viscosity. Light crude oil is liquid petroleum that has low viscosity, low specific gravity, and high API (American Petroleum Institute) gravity due to the presence of a high proportion of light hydrocarbon fractions. API gravity is calculated by dividing 141.5 by the fluid's specific gravity and subtracting 131.5. The New York Mercantile Exchange (NYMEX) defines light crude oil for domestic U.S. oil as having an API gravity between 37° API (840 kg/m3) and 42° API (816 kg/m3), while it defines light crude oil for non-U.S. oil as being between 32° API (865 kg/m3) and 42° API (816 kg/m3). The National Energy Board of Canada defines light crude oil as having a density less than 875.7 kg/m3 (more than 30.10 API). The Mexican state oil company, Pemex, defines light crude oil as being between 27° API (893 kg/m3) and 38° API (835 kg/m3). Unlike light crude oil, heavy crude oils are generally not pumpable due to the high viscosity. Therefore, it is advantageous to remove the higher viscosity products, i.e. asphaltenes, in order to pump the remaining, lighter de-asphalted crude oil. Light crude oil is also desired over heavy crude oil because it receives a higher price than heavy crude oil on commodity markets because it produces a higher percentage of gasoline and diesel fuel when converted into products by an oil refinery (see more in NDT patent).

Sonication is the act of applying sound energy to agitate particles in a sample, for various purposes. Ultrasonic frequencies (>20 kHz) are usually used, leading to the process also being known as ultrasonication or ultra-sonication "Sonication" and "low frequency acoustic sonication" refer hereinafter inter alia and in a non-limiting manner to methods whereby a material is subjected to low frequency acoustic vibration. Devices for producing such vibration, "sonicators", are disclosed in, for example, U.S. Pat. Nos. 4,941,134 and 5,005,773 (Nyberg et al.). Unlike ultrasonic devices, these low frequency sonic reactors are reducible to large scale commercial practice (e.g. 20 kilowatt sonicator modules) and can achieve HCO deasphalting at low solvent: HCO doses (with ultra-low residence times in the sonicator (e.g. less than 120 seconds), see Petrosonic patent below, which is incorporated herein as a reference.

EP 1276833 patent application by Foxboro NMR, Ltd. which is incorporated herein as a reference discloses a method for blending two or more constituents into a petroleum mixture employs nuclear magnetic resonance to obtain real-time estimates of selected properties of at least one of the constituents. A multivariate controller processes these estimates to determine the relative amounts of each constituent that are required to form a petroleum mixture having desired values of those selected properties.

EP 2584381 patent application by a ENI S.p.A. which is incorporated herein as a reference, discloses method for predicting the properties of crude oils by the application of neural networks articulated in phases and characterized by determining the T2 NMR relaxation curve of an unknown crude oil and converting it to a logarithmic relaxation curve; selecting the values of the logarithmic relaxation curve lying on a characterization grid; entering the selected values as input data for a multilayer neural network of the back propagation type, trained and optimized by means of genetic algorithms; predicting, by means of the trained and optimized neural network, the physico-chemical factors of the unknown crude oil.

The available publications "NMR properties of petroleum reservoir fluids" by G. J. Hirasaki, Sho-Wei Lo, Y. Zhang (currently available in http://www.researchgate.net/publication/10670196_NMR_properties_of_petroleum_reservoir_fluids/links/00b7d52a880594cfa5000000.pdf); and Maddinelli, G., L. Del Gaudio, and U. Cornaro. "Characterization of petrochemical products by the application of a mobile NMR instrument." Magnetic Resonance Imaging 25.4 (2007): 571, are incorporated herein as a reference US 20120305383 by Sorokin (Sorokin patent) which is incorporated herein as a reference discloses a process and a device, for the treatment of crude oil, component(s) of crude, or mixtures thereof, to convert components of said hydrocarbon liquid to products having boiling points that are lower than the boiling points of said components prior to treatment. The process comprises subjecting crude to be treated to ultrasound vibrations and to an electromagnetic field emitted by a an electromagnetic field generator; wherein the electromagnetic field emitted by said electromagnetic field generator comprises a component of electromagnetic field modulated by an electromagnetic field emitted from the crude to be treated on the exposure thereof to ultrasound vibrations. Sorokin patent is concerned with a method and a device for the processing of crude oil, components of crude, or mixtures thereof to increase the light hydrocarbon content thereof. Thus, Sorokin suggests a process for the treatment of crude oil, component(s) of crude, or mixtures thereof, wherein the novel concept is that the electromagnetic field emitted by an (a) electromagnetic field generator or (b) a ultrasound generator comprises a component of electromagnetic field modulated by an electromagnetic field emitted from the crude to be treated on the exposure thereof to ultrasound vibrations.

WO 2013110944 patent application by Nov Downhole Eurasia Limited and University Of Nottingham (Nov patent) which is incorporated herein as a reference discloses an apparatus for separating a hydrocarbon content from a material matrix comprises the hydrocarbon content and a water content, the apparatus comprising: a material feeder arranged to feed material through a treatment chamber, the treatment chamber comprising a window which is substantially transparent to microwaves; a microwave emitter arranged in use to expose feed material in the treatment chamber to microwaves via the window in order to cause rapid heating of at least part of the water content of the matrix to form steam, so as to remove at least part of the hydrocarbon content from the matrix; wherein the material feeder and treatment chamber are arranged so that in use, the treatment chamber is substantially filled with material matrix. The problem to solve of the invention is that hydrocarbons are often mixed within a matrix of other solid materials such as sand, soil or rock, and it is frequently desirable to separate or remove the hydrocarbons from such a matrix. For example, a substantial fraction of the world's hydrocarbon reserves are to be found in oil sands and in order to extract the oil, it must first be separated from the sand with which it is mixed.

US 20130277275 by Petrosonic Energy Inc. (Petrosonic patent) discloses a method for treating heavy crude oil (HCO) which includes the steps of combining the HCO with an alkane containing solvent to form an HCO/solvent mixture, sonicating this mixture at audio frequency to precipitate asphaltenes from the HCO/solvent mixture, and separating the precipitated asphaltenes from the HCO/solvent mixture.

Similarly, U.S. Pat. No. 8,323,479 patent discloses a process for converting heavy sulfur-containing crude oil into lighter crude oil with lower sulfur content and lower molecular weight is provided. The process is a low-temperature process using controlled cavitation. Patent application US2002125174 describes a method for decreasing the viscosity of crude oils and residuum utilizing a combination of acid and sonic treatment. Patent application US2013213795A describes conversion of heavy fossil hydrocarbons (HFH) to a variety of value-added chemicals and/or fuels can be enhanced using microwave (MW) and/or radiofrequency (RF) energy. Variations of reactants, process parameters, and reactor design can significantly influence the relative distribution of chemicals and fuels generated as the product. In one example, a system for flash microwave conversion of HFH includes a source concentrating microwave or RF energy in a reaction zone having a pressure greater than 0.9 Atm., a continuous feed having HFH and a process gas passing through the reaction zone, a HFH-to-liquids catalyst contacting the HFH in at least the reaction zone, and dielectric discharges within the reaction zone. The HFH and the catalyst have a residence time in the reaction zone of less than 30 seconds. In some instances, plasma forms in or near the reaction zone. U.S. Pat. No. 5,181,998 patent describes low value hydrocarbons can be upgraded by contact with the products formed during irradiation of a hydrogen donor using microwave energy in the presence of at least one plasma initiator. All those patents and applications are incorporated herein as a reference.

It is hence still a long felt need to provide industrial scale, inline, online accurate NMR-based systems for crude oil enhancement and to methods thereof.

BRIEF DESCRIPTION OF THE DRAWINGS

The disclosure may be better understood by reference to the detailed description when considered in conjunction with the accompanying drawings. The components and figures are not necessarily drawn to scale, emphasis being placed instead upon illustrating the principles of the disclosure.

DETAILED DESCRIPTION OF THE PREFERRED EMBODIMENTS

Figure 1:
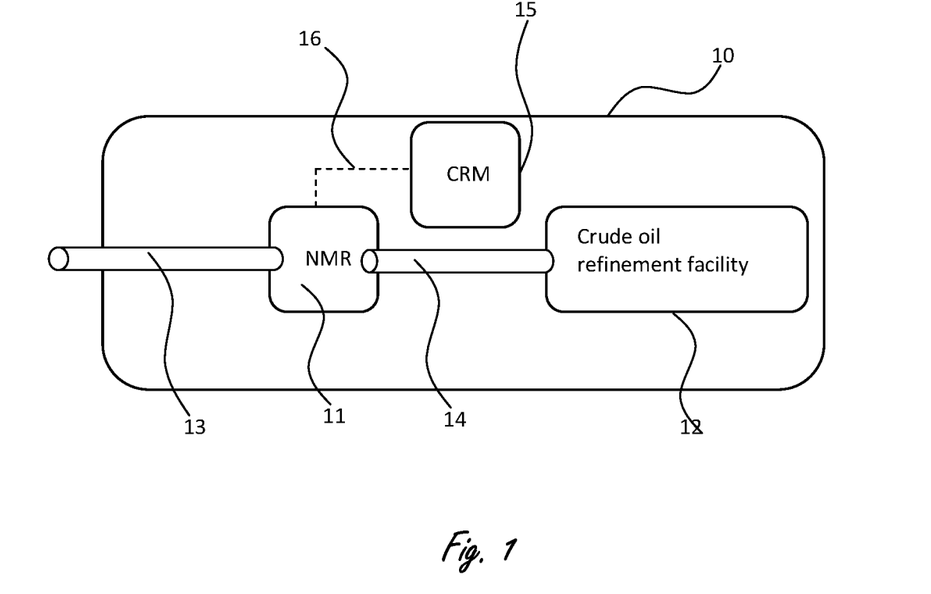
FIG. 1 illustrates a schematic block diagram of an NMR-based system in accordance with one embodiment of the disclosure.

Reference is now made to FIG. 1, illustrating a schematic block diagram of an NMR-based system (10) useful for analyzing one or more of the following: (i) crude oil property, (ii) crude oil rheology of crude oil. System (10) comprising an NMR device (11) configured for providing time and/or batch resolved NMR-analysis and/or crude oil rheological profile. The NMR having one or more crude oil inflow pipes (13), and is in a fluid connection (14) with a crude oil refinery facility (12). The improvement is that the said system further comprising or otherwise is in communication (16) with a computer readable medium (CRM, 15), configured to store a retrievable crude oil NMR analysis and/or crude oil rheological profile of a desired crude oil product (standard crude oil product, SCOP), thereby providing the system means to compare or otherwise validate NMR analysis and/or crude oil rheological profile of the SCOP with said time or batch resolved crude oil.

Figure 2:
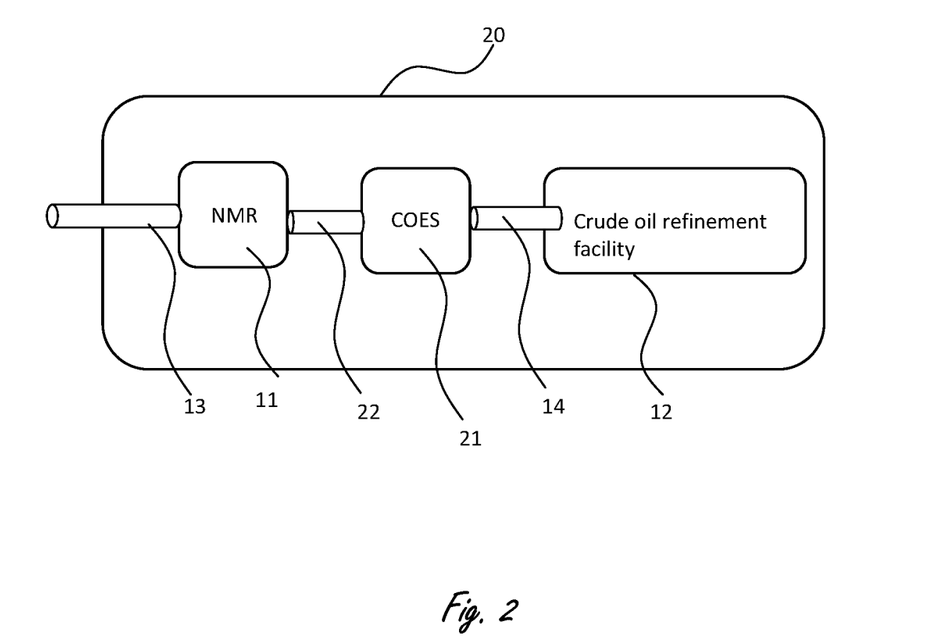
FIG. 2 illustrates a schematic block diagram of an NMR-based system in accordance with another embodiment of the disclosure.
Figure 3A:
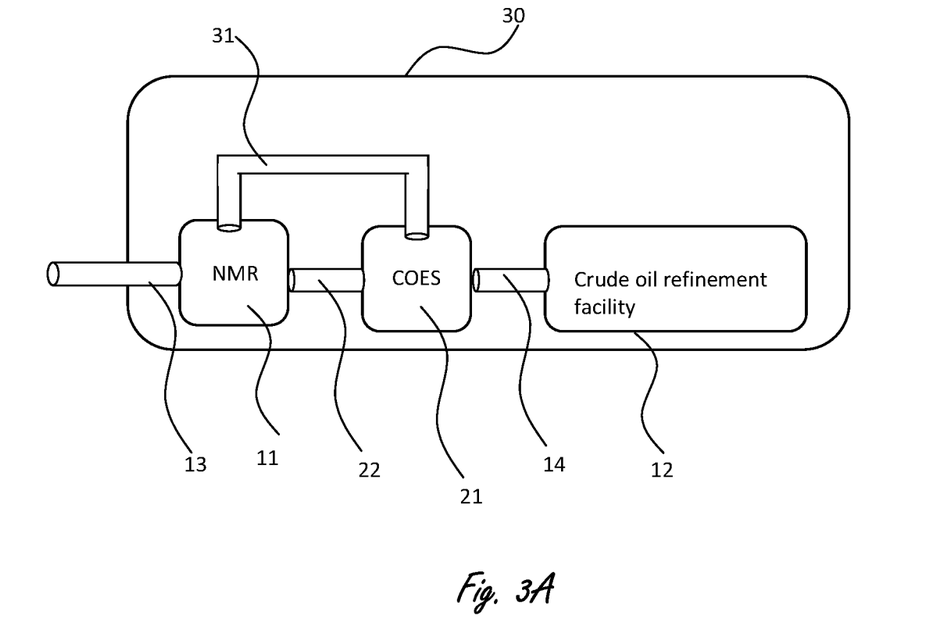
FIG. 3A illustrates a schematic block diagram of an NMR-based system in accordance with another embodiment of the disclosure.

Reference is now made to FIG. 2, illustrating a schematic block diagram NMR-based system (20) useful for both (a) analyzing one or more of the following: (i) crude oil property, (ii) crude oil rheology of crude oil; and (b) enhancing crude oil. The system comprises an NMR device (11) for providing time and/or batch resolved NMR analysis and/or crude oil rheological profile. The NMR is having at least one crude oil inflow pipe (13), and is in a fluid connection (14) with a crude oil refinery facility (12). The system further comprising a computer readable medium configured to store a retrievable crude oil NMR analysis and/or crude oil rheological profile of a desired crude oil product (standard crude oil product, SCOP), thereby providing the system means to compare NMR analysis and/or crude oil rheological profile of said SCOP with said time or batch resolved crude oil. The improvement here is that the system further comprising a crude oil enhancement system (COES) interconnected via at least one NMR crude oil outlet (22) to said NMR or a plurality of NMRs. The COES adapted for cracking of hydrocarbon oils thereby enhancing its property. Reference is now made to FIG. 3A, illustrating a schematic block diagram of an industrial scalable, inline, online accurate NMR-based system for crude oil enhancement and to methods thereof an NMR-based system (30)

useful for both (a) analyzing one or more of the following: (i) crude oil property, (ii) crude oil rheology of crude oil; and (b) enhancing crude oil. The system comprising, inter alia, an NMR device (11) for providing time and/or batch resolved NMR analysis and/or crude oil rheological profile. The NMR having a crude oil inflow pipe (13), and is in a fluid connection (14) with a crude oil refinery facility (12). The system further comprises a computer readable medium configured to store a retrievable crude oil NMR analysis and/or crude oil rheological profile of a desired crude oil product (standard crude oil product, SCOP), thereby providing the system means to compare NMR analysis and/or crude oil rheological profile of the SCOP with said time or batch resolved crude oil. The system further comprises a crude oil enhancement system (COES) interconnected via at least one NMR crude oil outlet (22) to the NMR. The COES adapted for cracking of hydrocarbon oils thereby enhancing its property. The improvement here is that the NMR further comprising COES-processed-crude-oil-outlet (COES-O, 31) in fluid connection with the COES.

Figure 3B:
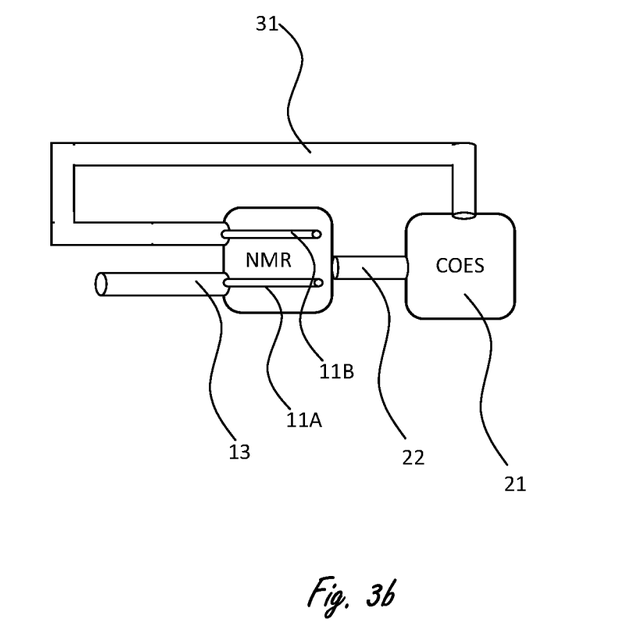
FIG. 3B illustrates a schematic block diagram of an NMR-based system in accordance with yet another embodiment of the disclosure.

Reference is now made to FIG. 3B, illustrating a schematic block diagram of an NMR-based system (30) as defined above, wherein the NMR (or NMRs) comprises at least one first probe (11A) and at least one second probe (11B). Those two (or more) NMR-probes thereby configuring the NMR to provide a time-resolved or batch-resolved NMR analysis and/or rheological profile of crude oil flowing in the at least one first and at least one second probes, concurrently (probe 1 and probe 2 together, at the same time) or interchangeably (probe 1 and then probe 2, and vice versa).

It is in the scope of the invention wherein the NMR-based system comprises at least one second probe which is configured to provide a time-resolved or batch resolved NMR analysis and/or rheological profile of the COES' processed recycled crude oil.

It is also in the scope of the invention wherein an NMR-based system is configured for analyzing and enhancing of crude oil. This system is characterized by an NMR which is provided in a fluid connection with both a crude oil inlet (COI) and crude oil outlet (COO); and a crude oil enhancement system (COES) interconnected to the NMR via said COO. The NMR comprises, inter alia, at least one first probe in fluid connection with said CO, and is configured for analyzing crude oil properties within said probe and/or for profiling said crude oil's rheology. The COES comprises, inter alia, one or more members of a group consisting of electric inducer, electromagnetic or mechanical vibrator, particle radiation emitter, gases super-heater in electric arcs, sonicator, ultrasound vibrations generator, radiofrequency emitter (e.g., RF radiation having a frequency between 0.1 MHz to 300 MHz) and any combination thereof.

It is further in the scope of the invention wherein the NMR-based system is configured for analyzing and enhancing a property of crude oil before oil refinery and the system characterized by (a) an NMR comprising at least one first probe configured to enable NMR analysis and/or rheological profile of crude oil, said probe is in a fluid connection with both NMR's crude oil inlet (NMR-I) and NMR's crude oil outlet (NMR-O); and by (b) a crude oil enhancement system (COES). COES comprises one or more crude oil cracking modules, selected from a group consisting of electric inducer, electromagnetic or mechanical vibrator, particle radiation emitter, gases super-heater in electric arcs, sonicator, ultrasound vibrations generator, radiofrequency emitter and any combination thereof (COCMs), at least one of said COCMs is in fluid connection with said NMR-O and NMR-I.

It is also in the scope of the invention wherein the NMR further comprising at least one second probe, thereby configuring the same to provide a time-resolved NMR analysis and/or rheological profile of crude oil flowing in said at least one first and at least one second probes, concurrently or interchangeably.

It is also in the scope of the invention wherein the at least one second probe is configured to provide a time-resolved NMR analysis and/or rheological profile of said processed recycled crude oil.

Figure 4:
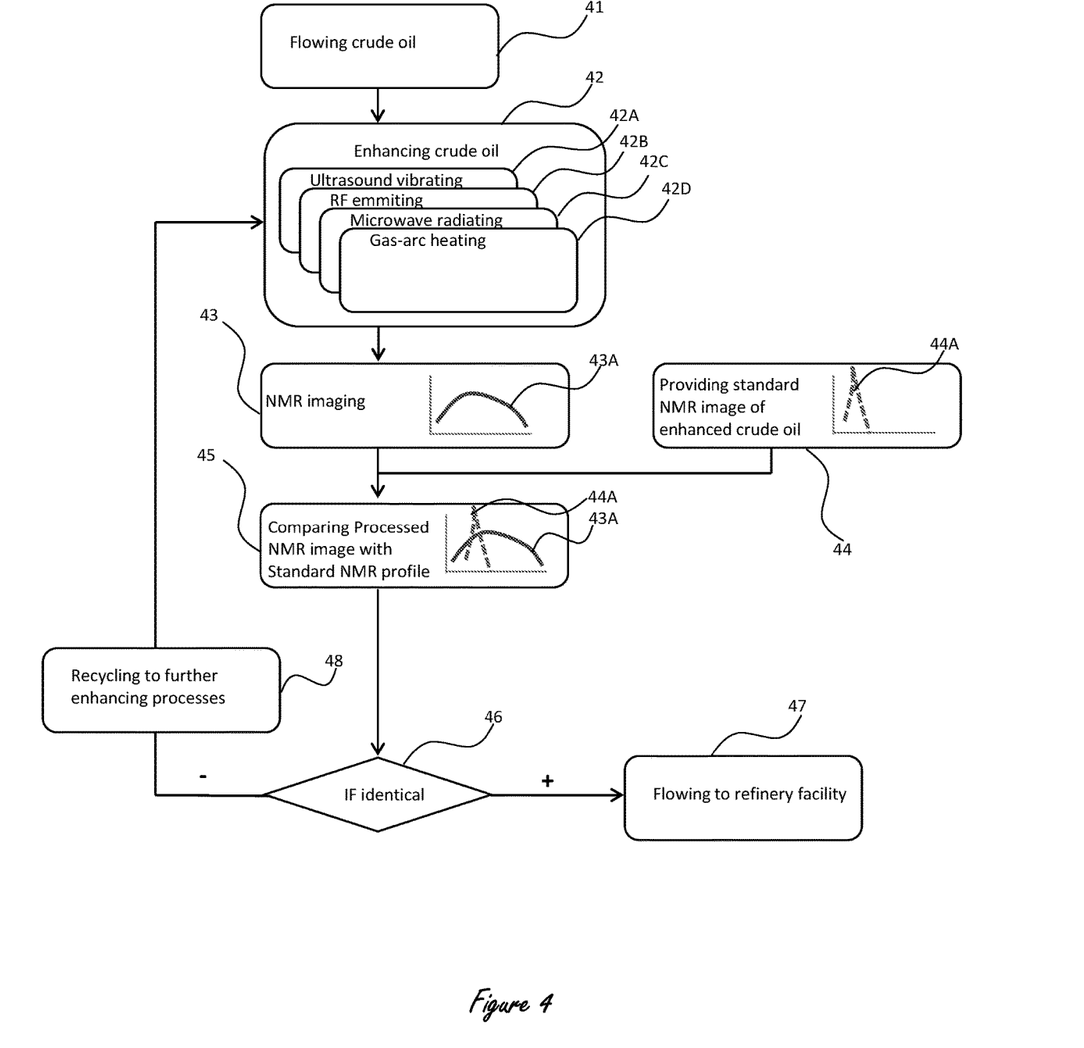
FIG. 4 illustrates a flowchart of a method for enhancing crude oil in accordance with an embodiment of the disclosure.

Reference is now made to FIG. 4, schematically illustrating a flow chart of a method for enhancing crude oil. The method comprising steps as follows: (a) proving an NMR in fluid connection with a crude oil enhancement system (COES) via both NMR crude oil outlet (NMR-O) flowing analyzed crude oil from said NMR to said COES, and a COES crude oil outlet (COES-O) recycling processed crude oil form said COES to NMR inlet; (b) storing, by means of computer readable medium, NMR analysis and/or rheological profile of a desired crude oil product processed in said COES (standard crude oil product); (c) providing said COES with at least one crude oil cracking module (COCM) and connecting the same with said NMR by means of said NMR-O; (d) processing said analyzed crude oil by means of said at least one COCM; (e) recycling at least a portion of said processed crude oil from said COES to said NMR via said COCM-O; (f) imaging said processed crude oil proving its NMR analysis and/or rheological profile; (g) comparing the NMR analysis and/or rheological profile of said standard crude oil product (of step b) with said processed crude oil (of step f); and (h) if said NMR analysis and/or rheological profile are identical or set within predefined limits, flowing said crude oil to refinery; if said NMR analysis and/or rheological profile are not identical or set outside predefined limits, recycling said crude oil to further processing by said COES.

It is in the scope of the invention wherein aforesaid step (a) further comprising step or steps for providing said NMR with at least one first probe and configuring the same for a time-resolved analyze of crude oil; and at least one second probe, and configuring the same for a time-resolved analyze of crude oil; flowing in said at least one first and at least one second probes and imaging the same concurrently or interchangeably.

It is in the scope of the invention wherein the method further comprising step of configuring said second probe to provide a time-resolved NMR analysis and/or rheological profile of said processed recycled crude oil.

It is also in the scope of the invention wherein a method for providing time and/or batch resolved NMR analysis and/or crude oil rheological profile is provided. The method comprises steps as follows: (a) providing an NMR having a crude oil inflow pipe (13) and a fluid connection (14) with a crude oil refinery facility (12); (b) providing a computer readable medium configured to store a retrievable crude oil NMR analysis and/or crude oil rheological profile of a desired crude oil product; and (c) comparing said oil NMR analysis and/or crude oil rheological profile of a desired crude oil product with said time and/or batch resolved NMR analysis and/or crude oil rheological profile.

It is also in the scope of the invention wherein a method for providing time and/or batch resolved NMR analysis and/or crude oil rheological profile is provided. The method comprises steps as follows: (a) providing an NMR having a crude oil inflow pipe (13) and a fluid connection (14) with a crude oil refinery facility (12); (b) further providing a computer readable medium configured to store a retrievable crude oil NMR analysis and/or crude oil rheological profile of a desired crude oil product; (c) further providing a crude oil enhancement system (COES) interconnected via NMR crude oil outlet (22) to said NMR; (d) comparing said oil NMR analysis and/or rheological profile of said desired crude oil product with said time and/or batch resolved NMR analysis and/or crude oil rheological profile; and (e) cracking said crude oil according to the degree of resemblance of said batch resolved NMR analysis and/or crude oil rheological profile with said NMR analysis and/or rheological profile of said desired crude oil product.

It is also in the scope of the invention wherein a method for providing time and/or batch resolved NMR analysis and/or crude oil rheological profile is provided. The method comprises steps as follows: (a) providing an NMR having a crude oil inflow pipe (13) and a fluid connection (14) with a crude oil refinery facility (12); (b) further providing a computer readable medium configured to store a retrievable crude oil NMR analysis and/or crude oil rheological profile of a desired crude oil product; (c) further providing a crude oil enhancement system (COES) interconnected via NMR crude oil outlet (22) to said NMR and further comprising COES-processed-crude-oil-outlet (COES-O, 31) in fluid connection with said NMR; (d) comparing said oil NMR analysis and/or rheological profile of said desired crude oil product with said time and/or batch resolved NMR analysis and/or crude oil rheological profile; and (e) cracking said crude oil according to the degree of resemblance of said batch resolved NMR analysis and/or crude oil rheological profile with said NMR analysis and/or rheological profile of said desired crude oil product. It is also in the scope of the invention wherein this method additionally comprising a step of providing said NMR at least one first probe (11A) and at least one second probe (11B), thereby configuring said NMR to provide a time-resolved NMR analysis and/or rheological profile of crude oil flowing in said at least first and at least one second probes, concurrently or interchangeably. It is also in the scope of the invention wherein this method additionally comprising a step of configuring said second probe to provide a time-resolved NMR analysis and/or rheological profile of said processed recycled crude oil.

It is in the scope of the invention wherein the methods and systems defined above are configured to enable ANSI/ISA 76.00.02-2002 Modular Component Interfaces for Surface-Mount Fluid Distribution Components—Part 1: Elastomeric Seals," Instrumentation, Systems, and Automation Society (ISA), Compositional Analyzers Committee, (2002).

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures and the detailed description that follow more particularly exemplify these embodiments.

The invention claimed is:

1. An NMR-based system to analyze a property of crude oil, the system comprising: an NMR device in fluid communication with a crude oil refinery facility, wherein the NMR device is configured to generate at least one of a time-resolved or batch-resolved NMR analysis of said crude oil and a crude oil rheological profile, a crude oil inflow pipe coupled to the NMR device; a computer readable medium configured to store at least one of a retrievable crude oil NMR analysis and a crude oil rheological profile of a desired crude oil product; and means for comparing the at least one of the retrievable crude oil NMR analysis and crude oil rheological profile of said desired crude oil product with said generated at least one of the time-resolved or batch-resolved NMR analysis of said crude oil and the crude oil rheological profile.

2. The NMR-based system of claim 1 further comprising a crude oil enhancement system (COES) coupled to said NMR device via a NMR crude oil outlet, wherein said COES is configured to generate processed recycled crude oil by cracking one or more hydrocarbon oils in said crude oil, thereby enhancing a property of said crude oil.

3. The NMR-based system of claim 2, further comprising at least one first probe and at least one second probe coupled to the NMR device, wherein the NMR device is configured to provide at least one of a time-resolved NMR analysis and rheological profile of said crude oil flowing in said at least one first and at least one second probes, concurrently or interchangeably.

4. The NMR-based system of claim 3, wherein said NMR device is configured to provide at least one of a time-resolved NMR analysis and a rheological profile of said processed recycled crude oil.

5. The NMR-based system of claim 1, wherein the desired crude oil product is a standard crude oil product.

6. An NMR-based system configured for analyzing and enhancing crude oil, the system comprising:
   an NMR device in fluid connection with both a crude oil inlet (COI) and crude oil outlet (COO);
   a crude oil enhancement system (COES) interconnected to said NMR device via said COO;
   at least one first probe in fluid connection with said COI, wherein the NRM device is configured to at least one of:
      analyze at least one of properties of said crude oil within said probe; and
      profile the rheology of said crude oil within said probe
   wherein the COES comprising one or more members of: of an electric inducer, an electromagnetic vibrator, a mechanical vibrator, a particle radiation emitter, ga ases super-heater in electric arcs, a sonicator, an ultrasound vibrations generator, and a radiofrequency emitter, and is configured to generate processed recycled crude oil by enhancing a property of said crude oil based on a comparison of at least one of said NMR analysis and said rheology profile to at least one of a crude oil NMR analysis of a desired crude oil product and a crude oil rheological profile of a desired crude oil product.

7. The NMR-based system of claim 6, wherein the at least one first probe is in fluid connection with said COO.

8. The NMR-based system of claim 7, further comprising at least one second probe, wherein the NMR device is configured to provide at least one of a time-resolved NMR analysis and a rheological profile of crude oil flowing in said at least one first and at least one second probes, concurrently or interchangeably.

9. The NMR-based system claim 8, wherein said NMR device is configured to provide at least one of a time-resolved NMR analysis and rheological profile of said processed recycled crude oil.

10. A method for enhancing crude oil comprising:
    imaging the crude oil, using an NRM device, to generate analyzed crude oil;

processing said analyzed crude oil, using a crude oil enhancement system, to generate processed recycled crude oil;

generating, using the NMR device, at least one of an NMR analysis and a rheological profile of said processed recycled crude oil;

comparing the generated at least one of NMR analysis and the rheological profile of the recycled processed crude oil with at least one of a NMR analysis and a rheological profile of a desired crude oil product;

causing the processed recycled crude oil to flow to a refinery if said generated at least one of the NMR analysis and the rheological profile of the processed recycled crude oil is identical or within predefined limits of the at least one of the NMR analysis and the rheological profile of the desired crude oil product;

further processing the processed recycled crude oil, using the COES, if said generated at least one of the NMR analysis and the rheological profile of tine processed recycled crude oil is not identical or outside predefined limits of the at least one of the NMR analysis and the rheological profile of the desired crude oil product.

11. The method of claim 10, wherein imaging the crude oil, using an NRM device, to generate analyzed crude oil comprises using at least one first probe and one second probe to generate at least one of a time-resolved NMR analysis and rheological profile of said crude oil flowing in said at least one first and at least one second, probes, concurrently or interchangeably.

12. The NMR-based system of claim 11, further comprising configuring said second probe to provide at least one of a time-resolved NMR analysis and a rheological profile of said processed recycled crude oil.

13. The method of claim 10, wherein processing said analyzed crude oil comprises cracking one or more hydrocarbon oils within the analyzed crude oil using a crude oil cracking module.

* * * * *